US011560463B2

(12) United States Patent
Lim et al.

(10) Patent No.: US 11,560,463 B2
(45) Date of Patent: Jan. 24, 2023

(54) CROSS-LINKING AGENT COMPOUND AND POLYMER PREPARED USING THE SAME

(71) Applicant: LG Chem, Ltd., Seoul (KR)

(72) Inventors: Won Taeck Lim, Daejeon (KR); Wonmun Choi, Daejeon (KR); Gicheul Kim, Daejeon (KR); Ki Hyun Kim, Daejeon (KR)

(73) Assignee: LG Chem, Ltd.

( * ) Notice: Subject to any disclaimer, the term of this patent is extended or adjusted under 35 U.S.C. 154(b) by 302 days.

(21) Appl. No.: 16/770,887

(22) PCT Filed: Nov. 20, 2018

(86) PCT No.: PCT/KR2018/014281
§ 371 (c)(1),
(2) Date: Jun. 8, 2020

(87) PCT Pub. No.: WO2019/112203
PCT Pub. Date: Jun. 13, 2019

(65) Prior Publication Data
US 2021/0115222 A1 Apr. 22, 2021

(30) Foreign Application Priority Data

Dec. 8, 2017 (KR) .................. 10-2017-0168683
Nov. 14, 2018 (KR) .................. 10-2018-0139993

(51) Int. Cl.
| C07C 69/54 | (2006.01) |
| C08K 5/11 | (2006.01) |
| C08F 20/06 | (2006.01) |
| C08K 5/00 | (2006.01) |
| C08F 220/06 | (2006.01) |
| C08F 120/06 | (2006.01) |
| C07C 69/602 | (2006.01) |

(52) U.S. Cl.
CPC .............. C08K 5/11 (2013.01); C07C 69/54 (2013.01); C07C 69/602 (2013.01); C08F 20/06 (2013.01); C08F 120/06 (2013.01); C08F 220/06 (2013.01); C08K 5/0025 (2013.01)

(58) Field of Classification Search
CPC ...... C08F 20/06; C08F 120/06; C08F 220/06; C08K 5/0025; C08K 5/103; C07C 69/54; C07C 69/602
See application file for complete search history.

(56) References Cited

U.S. PATENT DOCUMENTS

| 2,877,205 A | 3/1959 | Joginder |
| 5,281,683 A | 1/1994 | Yano et al. |
| 5,840,804 A * | 11/1998 | Carl .................. C02F 1/56 |
| | | 524/832 |
| 9,701,796 B2 | 7/2017 | Jung et al. |

| 2003/0065047 A1 * | 4/2003 | Katou ............. C09D 4/06 |
| | | 522/1 |
| 2004/0180189 A1 | 9/2004 | Funk et al. |
| 2007/0015860 A1 | 1/2007 | Frank |
| 2008/0075937 A1 | 3/2008 | Wada et al. |
| 2008/0140037 A1 | 6/2008 | Newman |
| 2010/0234531 A1 | 9/2010 | Frank |
| 2013/0172180 A1 | 7/2013 | Naumann et al. |
| 2014/0220279 A1 | 8/2014 | Tsukada et al. |
| 2014/0312273 A1 | 10/2014 | Wattebled et al. |
| 2015/0037526 A1 | 2/2015 | Seth et al. |
| 2015/0217270 A1 | 8/2015 | Ueda et al. |
| 2015/0252130 A1 | 9/2015 | Loick et al. |
| 2016/0184799 A1 | 6/2016 | Lee et al. |
| 2016/0311985 A1 | 10/2016 | Jung et al. |
| 2017/0015798 A1 | 1/2017 | Lee et al. |
| 2017/0260303 A1 | 9/2017 | Chung et al. |
| 2018/0243464 A1 | 8/2018 | Hwang et al. |
| 2019/0085103 A1 | 3/2019 | Kim et al. |
| 2019/0125921 A1 | 5/2019 | Kimura et al. |
| 2020/0115508 A1 | 4/2020 | Lee et al. |

FOREIGN PATENT DOCUMENTS

| CN | 101094695 A | 12/2007 |
| CN | 103012901 A | 4/2013 |
| CN | 103797062 A | 5/2014 |
| CN | 104024291 A | 9/2014 |
| CN | 105555812 A | 5/2016 |
| CN | 105814088 A | 7/2016 |
| CN | 106164099 A | 11/2016 |
| CN | 107922636 A | 4/2018 |
| EP | 3067370 A1 | 9/2016 |
| EP | 3020737 A4 | 3/2017 |
| FR | 1387099 A | 1/1965 |
| GB | 1054279 A | 1/1967 |
| GB | 2280433 A | 2/1995 |
| JP | 2002121228 A | 4/2002 |

(Continued)

OTHER PUBLICATIONS

O'Brien, Polymer, 41 (2000) 6027-6031. (Year: 2000).*
Gorodetskaya, et al., Functionalized Hyperbranched Polymers via Olefin Metathesis, Macromolecules, Published on Web Mar. 2009, pp. 2895-2898, vol. 42, American Chemical Society.
International Search Report from Application No. PCT/KR2018/014281 dated Mar. 8, 2019, 2 pages.
International Search Report including Written Opinion from Application No. PCT/KR2018/014282 dated Mar. 8, 2019, pp. 1-8.
Kritskaya, et al., A Model of the Formation of Branched Polymethyl Methacrylates, Chemical Physics of Polymer Materials, Russian Journal of Physical Chemistry B, 2009, pp. 835-843, vol. 3, No. 5.

(Continued)

*Primary Examiner* — Robert C Boyle
(74) *Attorney, Agent, or Firm* — Lerner, David, Littenberg, Krumholz & Mentlik, LLP

(57) ABSTRACT

The present disclosure relates to a novel cross-linking agent compound and a polymer prepared using the same. Specifically, the present disclosure relates to a cross-linking agent compound having a novel structure and excellent in cross-linking and pyrolysis, and a polymer prepared using the same.

10 Claims, No Drawings

(56) References Cited

FOREIGN PATENT DOCUMENTS

| | | |
|---|---|---|
| JP | 2004123611 A | 4/2004 |
| JP | 2004530777 A | 10/2004 |
| JP | 2006116535 A | 5/2006 |
| JP | 2006528708 A | 12/2006 |
| JP | 2008522003 A | 6/2008 |
| JP | 2016521306 A | 7/2016 |
| JP | 2016537490 A | 12/2016 |
| JP | 2017502108 A | 1/2017 |
| JP | 2017185485 A | 10/2017 |
| JP | 2020516753 A | 6/2020 |
| KR | 950008724 B1 | 8/1995 |
| KR | 20110082518 A | 7/2011 |
| KR | 20140094536 A | 7/2014 |
| KR | 20140104536 A | 9/2015 |
| KR | 20160071250 A | 6/2016 |
| KR | 20160117180 A | 10/2016 |
| KR | 101700907 B1 | 1/2017 |
| KR | 20180043143 A | 4/2018 |
| WO | 2008093507 A1 | 8/2008 |
| WO | 2010040466 A1 | 4/2010 |
| WO | 2014034897 A1 | 3/2014 |
| WO | 2016159600 A1 | 10/2016 |
| WO | 2017170501 A1 | 10/2017 |

OTHER PUBLICATIONS

O'Brien, et al., Facile, versatile and cost effective route to branched vinyl polymers, Polymer, 2000, pp. 6027-6031, vol. 41.

Odian, Principles of Polymerization, 1981, p. 203, Second Edition, John Wiley & Sons.

Schwalm, UV Coatings Basics Recent Developments and New Applications, Dec. 2006, p. 115, Elsevier Science.

Extended European Search Report including Written Opinion for EP18885147.1 dated Oct. 8, 2020; 7 pages.

Search Report from Chinese Office Action for Application No. 2018800246633 dated Sep. 29, 2020; 2 pages.

Search Report from Registered Search Organization dated Nov. 25, 2020; 8 pages.

Chinese Search Report for Application No. 201880078028.3 dated May 8, 2021, 2 pages.

* cited by examiner

CROSS-LINKING AGENT COMPOUND AND POLYMER PREPARED USING THE SAME

CROSS-REFERENCE TO RELATED APPLICATIONS

The present application is a national phase entry under 35 U.S.C. § 371 of International Application No. PCT/KR2018/014281 filed Nov. 20, 2018, which claims priority to Korean Patent Application No. 10-2017-0168683 filed on Dec. 8, 2017, and Korean Patent Application No. 10-2018-0139993 filed on Nov. 14, 2018 with the Korean Intellectual Property Office, the disclosures of which are incorporated herein by reference in their entirety.

BACKGROUND OF THE INVENTION

(a) Field of the Invention

The present disclosure relates to a novel cross-linking agent compound and a polymer prepared using the same. Specifically, the present disclosure relates to a cross-linking agent compound having a novel structure and excellent in cross-linking and pyrolysis, and a polymer prepared using the same.

(b) Description of the Related Art

A super absorbent polymer (SAP) is a type of synthetic polymeric material capable of absorbing 500 to 1000 times its own weight of moisture. Various manufacturers have denominated it with different names, such as SAM (Super Absorbency Material), AGM (Absorbent Gel Material), and the like. Such super absorbent polymers started to be practically applied in sanitary products, and they are now being widely used not only for hygiene products such as disposable diapers for children, etc., but also for water retaining soil products for gardening, water stop materials for the civil engineering and construction, sheets for raising seedling, fresh-keeping agents for food distribution fields, materials for poultices, or the like.

In most cases, the super absorbent polymer is widely used in the field of hygiene products such as diapers and sanitary napkins, and, for this purpose, it is necessary to exhibit a high absorption capacity for moisture and the like. In addition, it is necessary that the absorbed moisture should not leak out even under external pressure. Further, it needs to show excellent permeability by maintaining its shape even in an expanded (swelled) state after absorbing water.

Therefore, in order for the super absorbent polymer to have excellent performance, the base resin, which is the most important constituent polymer, should have high absorption ability.

In order to prepare the base resin, generally, internal cross-linking density of the polymer can be controlled by polymerizing an acrylic acid-based monomer in the presence of an internal cross-linking agent. The internal cross-linking agent is used for cross-linking the interior of a polymer in which an acrylic acid-based monomer is polymerized, that is, a base resin, and the internal cross-linking density of the base resin can be controlled according to the type and content of the internal cross-linking agent. When the cross-linking density of the base resin is low, the absorption ability is increased but strength is weak, so that the shape cannot be maintained in the subsequent steps. When the cross-link density is too high, strength is increased but the water absorption ability may be deteriorated. Therefore, it is very important to control the cross-linking density appropriately in view of the strength and the absorption ability of the base resin.

Further, the super absorbent polymer prepared by polymerizing an acrylic acid-based monomer has a characteristic odor of acrylic acid, and when it is used for hygiene products such as diapers, it is accompanied with an unpleasant odor when urine or the like is excreted. Therefore, effectively reducing these odors is required. For this purpose, a method of using a porous adsorbent material in combination with a super absorbent polymer has been developed.

When the porous adsorbent material is mixed with the super absorbent polymer, the odor can be reduced. However, there is a problem in that physical properties of the super absorbent polymer such as absorption ability and permeability are deteriorated, or caking phenomenon occurs in which the super absorbent polymer aggregates or hardens with time.

SUMMARY OF THE INVENTION

The present disclosure has been developed to solve the above problem, and to provide a cross-linking agent compound having a novel structure and a polymer prepared using the cross-linking agent compound. The cross-linking agent compound is excellent in cross-linking, pyrolysis and odor characteristics, and may be used as a cross-linking agent in the preparation of a super absorbent polymer.

According to one embodiment of the present disclosure, provided is a cross-linking agent compound represented by the following Chemical Formula 1:

[Chemical Formula 1]

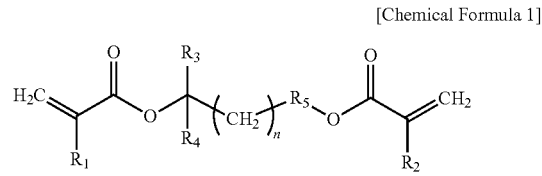

in Chemical Formula 1, $R_1$ and $R_2$ are each independently hydrogen or methyl, $R_3$ and $R_4$ are each independently hydrogen or a C1 to C20 alkyl, $R_5$ is a linear or branched C1 to C20 alkylene substituted with a linear or branched C2 to C10 alkenyl; or a linear or branched C2 to C20 alkenylene, and n is an integer of 0 to 10.

According to another embodiment of the present disclosure, provided is a polymer obtained by polymerizing the cross-linking agent compound and an acrylic acid-based monomer.

The cross-linking agent compound of the present disclosure has a novel structure not known in the prior art and includes a specific moiety. In addition, the polymer in which the cross-linking agent compound of the present disclosure and the acrylic acid-based monomer are polymerized is capable of pyrolysis in which the cross-linking structure is decomposed at a predetermined temperature or higher.

Therefore, the polymer prepared by using the cross-linking agent compound of the present disclosure may exhibit high cross-linking density immediately after polymerization and have high strength and excellent processability. Further, the polymer may have improved absorption ability as the internal cross-linking structure is decomposed in the subsequent high-temperature process and the cross-link density is lowered.

Further, due to the unique aroma of the cross-linking agent compound of the present disclosure, it is possible to provide deodorizing effect that reduces the odor peculiar to the super absorbent polymer and/or odors generated when used as hygiene products, and an excellent feeling of use with a natural aroma without any additional additive.

DETAILED DESCRIPTION OF THE EMBODIMENTS

As the present invention can be variously modified and have various forms, specific embodiments thereof are shown by way of examples and will be described in detail. However, it is not intended to limit the present invention to the particular form disclosed and it should be understood that the present invention includes all modifications, equivalents, and replacements within the idea and technical scope of the present invention.

Hereinafter, the cross-linking agent compound and the polymer prepared using the same will be described in more detail.

The Cross-Linking Agent Compound

The cross-linking agent compound is represented by the following Chemical Formula 1:

[Chemical Formula 1]

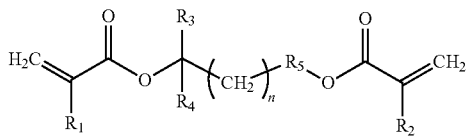

in Chemical Formula 1, $R_1$ and $R_2$ are each independently hydrogen or methyl, $R_3$ and $R_4$ are each independently hydrogen or a C1 to C20 alkyl, $R_5$ is a linear or branched C1 to C20 alkylene substituted with a linear or branched C2 to C10 alkenyl; or a linear or branched C2 to C20 alkenylene, and n is an integer of 0 to 10.

In the present disclosure, "alkyl" refers to a linear or branched saturated monovalent hydrocarbon having 1 to 20, preferably 1 to 10, more preferably 1 to 5 carbon atoms. Specific examples of the alkyl include methyl, ethyl, propyl, n-propyl, isopropyl, n-butyl, isobutyl, tert-butyl, sec-butyl, 1-methyl-butyl, 1-ethyl-butyl, n-pentyl, isopentyl, neopentyl, tert-pentyl, n-hexyl, isohexyl, 1-methylpentyl, 2-methylpentyl, 4-methyl-2-pentyl, 3,3-dimethylbutyl, 2-ethylbutyl, n-heptyl, 1-methylhexyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, 2-methylpentyl, 4-methylhexyl, 5-methylhexyl, and the like, but are not limited thereto.

In the present disclosure, "alkylene" refers to a linear or branched saturated divalent hydrocarbon having 1 to 20, preferably 1 to 10, more preferably 1 to 5 carbon atoms. Specific examples of the alkylene include methylene, ethylene, propylene, butylene, hexylene, heptylene, octylene and the like, but are not limited thereto.

In the present disclosure, "alkenyl" refers to a linear or branched monovalent hydrocarbon containing at least one carbon-carbon double bond having 2 to 20, preferably 2 to 10, more preferably 2 to 6 carbon atoms. The alkenyl may be bonded through a carbon atom containing a carbon-carbon double bond and/or through a saturated carbon atom. Specific examples of the alkenyl include allyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl and the like, but are not limited thereto.

In the present disclosure, "alkenylene" refers to a linear or branched divalent hydrocarbon containing at least one carbon-carbon double bond having 2 to 20, preferably 2 to 10, more preferably 2 to 6 carbon atoms. The alkenylene may be bonded through a carbon atom containing a carbon-carbon double bond and/or through a saturated carbon atom. Specific examples of the alkenylen include ethenylene, propenylene, butenylene and the like, but are not limited thereto.

The cross-linking agent compound of Chemical Formula 1 is a di(meth)acrylate derivative compound having a novel structure.

According to one embodiment of the present disclosure, the $R_1$ and $R_2$ may be hydrogen.

According to one embodiment of the present disclosure, the $R_3$ and $R_4$ may be a C1 to C5 alkyl. Preferably, the $R_3$ and $R_4$ may be methyl.

According to one embodiment of the present disclosure, the $R_5$ may be a linear or branched C1 to C10 alkylene substituted with a C2 to C10 alkenyl; or a linear or branched C2 to C10 alkenylene. For example, the $R_5$ may be 3-methyl-2-hexenylidene, 3-methyl-1-hexenylidene, 4,8-dimethylundeca-3,7-dienylene, and the like, but the present disclosure is not limited thereto.

According to one embodiment of the present disclosure, n may be an integer of 0 to 10. Preferably, n may be 0 to 5, or 0 to 3.

According to one embodiment of the present disclosure, the compound represented by the Chemical Formula 1 may be selected from the compounds represented by the following Chemical Formulae 1-1 to 1-3:

[Chemical Formula 1-1]

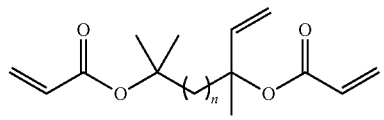

[Chemical Formula 1-2]

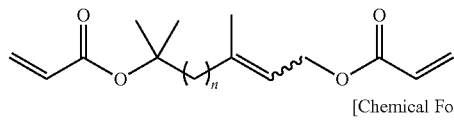

[Chemical Formula 1-3]

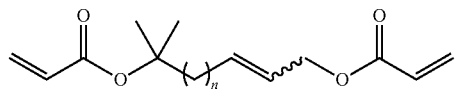

in Chemical Formulae 1-1 to 1-3, n is as defined in the Chemical Formula 1.

The use of the compound represented by the Chemical Formula 1 is not limited thereto, but the compound may be used as a cross-linking agent in the polymerization with an acrylic acid-based monomer.

The cross-linking agent compound of the Chemical Formula 1 may be prepared by a known organic synthesis method, for example, by the following Reaction Scheme 1, but the present disclosure is not limited thereto.

[Reaction Scheme 1]

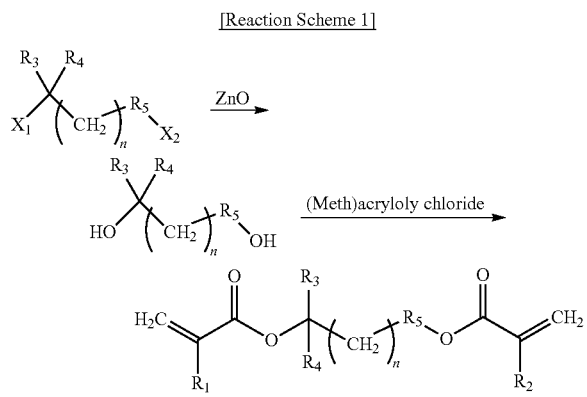

in Reaction Scheme 1, $R_1$ to $R_5$, and n are as defined in the Chemical Formula 1, and $X_1$ and $X_2$ are halogen.

According to one embodiment of the present disclosure, the compound of Chemical Formula 1 can be prepared by the following method, when it is the compound of Chemical Formula 1-1 or 1-2. But the present disclosure is not limited thereto.

First, a halogen group is introduced into a starting material of myrcene or geraniol. Next, a diol is prepared by substituting a halogen group with a hydroxy group. Then, an acryloyl group is introduced into the diol to obtain a mixture of the above formulae 1-1 and 1-2, and these are separated.

The myrcene and geraniol are derivative compounds of terpene. Terpenes are flammable, unsaturated hydrocarbons widely distributed in plants and animals, and are hydrocarbons having a general formula of $(C_5H_8)_k (k \geq 2)$. Terpenes are classified according to the number of isoprene $(C_5H_8)$ units in the molecule, and monoterpene $(C_{10}H_{16})$, sesquiterpene $(C_{15}H_{24})$ and diterpene $(C_{20}H_{32})$ have two, three and four isoprene units, respectively. Monoterpenes, sesquiterpenes, and diterpenes are found in essential oils of plants, and are used as raw materials for fragrance, medicines, and chemical industry. Also, terpenes, terpene alcohols, terpene aldehydes, terpene ketones, terpene oxides, terpene lactones and the like are collectively referred to as terpenoids.

Myrcene is a kind of monoterpenes, found in abundance in essential oils in many plants, including hops, lemon grass, thyme, verbena, and bay leaves, and has a unique herbal flavor.

Geraniol is a kind of monoterpenoids, and also included in many essential oils such as geranium and lemon. It is not soluble in water, but is easily soluble in most common organic solvents and has an aroma like a rose.

When the compound of Chemical Formula 1 is prepared by using a natural terpene such as myrcene or geraniol as a starting material, and this is used for cross-linking the polymer as a cross-linking agent, deodorizing effect can be ensured and a scent can be released without any additional additive, since the myrcene or geraniol gives off the original scent when the cross-linking agent is decomposed at a high temperature.

More specifically, according to one embodiment of the present disclosure, the cross-linking agent compounds of the Chemical Formulae 1-1 and 1-2 may be prepared by the following Reaction Schemes 2-1 and 3.

[Reaction Scheme 2-1]

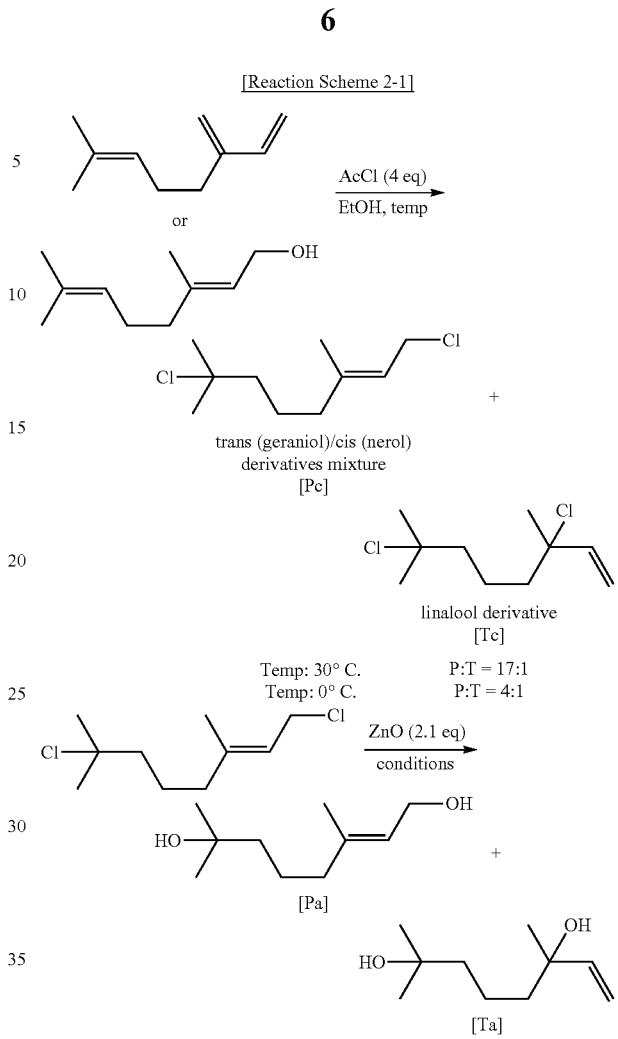

In Reaction Scheme 2-1, 1 equiv. of myrcene or geraniol is dissolved in ethanol and stirred. Acetic chloride (4 equiv.) is slowly added dropwise while maintaining a reaction temperature at 0 to 30° C. When the conversion and termination of the reaction to the dichloronate compounds are confirmed by TLC, the solvent and the unreacted materials are removed by evaporation under reduced pressure. The resulting dichloronate compounds (a mixture of Pc and Tc) are used in the next reaction without any further purification. The obtained dichloronate mixture is put into an acetone aqueous solution of about 80% purity, about 2.1 equiv. of zinc oxide (ZnO) is added, and the mixture is refluxed at a temperature of 100° C.

When the conversion and termination of the reaction to the diol compounds are confirmed by TLC, the temperature is cooled to room temperature. Thereafter, the solid precipitate is removed using a filtration filter, and the remaining acetone is removed by evaporation under reduced pressure. The remaining organic material and a small amount of water are removed by fractional distillation to obtain desired diol compounds (a mixture of Pa and Ta). When the diol compounds are prepared according to Reaction Scheme 2-1, it can be confirmed that the amount of Compound Ta is increased compared to that of Compound Pa.

Subsequently, an acryloyl group can be introduced into the above mixture of Pa and Ta by the following Reaction Scheme 3.

[Reaction Scheme 3]

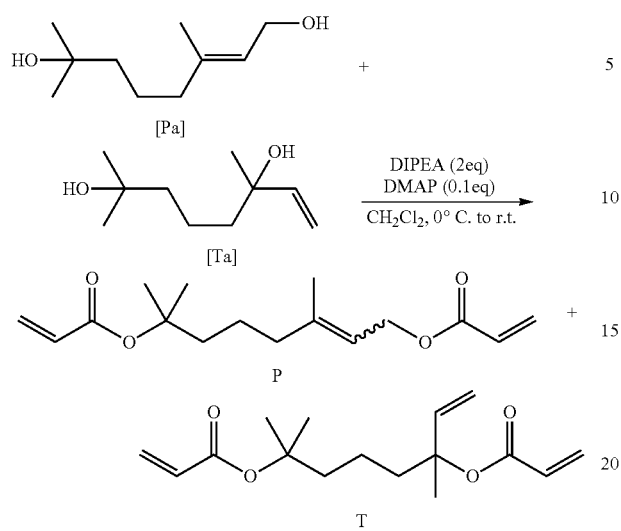

[Reaction Scheme 2-2]

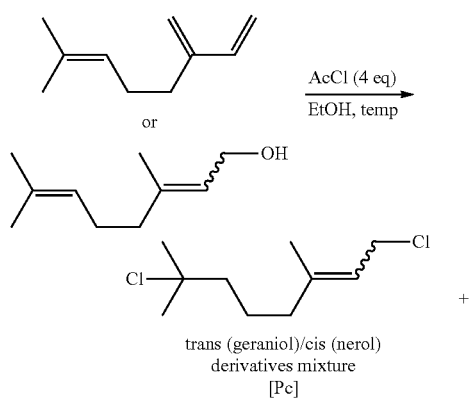

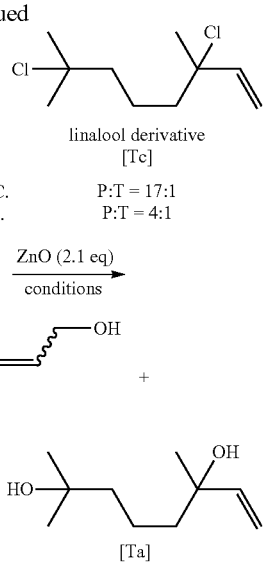

In Reaction Scheme 3, the mixture of Pa and Ta is dissolved in CH$_2$Cl$_2$ (1.0M) and the temperature is lowered to 0° C. while stirring. After 2 equiv. of triethylamine (TEA) or N,N-diisopropylethylamine (DIPEA) and 0.1 equiv. of 4-dimethylaminopyridine (DMAP) are added, 2 equiv. of acryloyl chloride is slowly added thereto. After the addition is completed, the reaction temperature is raised to room temperature and stirred for about 4 to about 12 hours. After the reaction is completed, the reaction solution is filtered through a celite pad and the solvent is removed under vacuum. The remaining organic materials are extracted with water and ethyl acetate, and the remaining water in the organic layer is removed using sodium sulfate (Na$_2$SO$_4$). The solids are filtered off and the remaining organic solvent is removed under vacuum to obtain desired P (the compound of Chemical Formula 1-2) and T (the compound of Chemical Formula 1-1).

The compounds of Chemical Formulae 1-1 and 1-2 obtained above may be used after separation and purification, or may be used in the form of a mixture without separation.

According to another embodiment of the present disclosure, the cross-linking agent compounds of the Chemical Formulae 1-1 and 1-2 may be prepared by the following Reaction Schemes 2-2 and 3.

In Reaction Scheme 2-2, the reaction up to the dichloronate compounds is performed in the same manner as in Reaction Scheme 1. Thereafter, in the reaction of replacing Cl with OH, the obtained dichloronate mixture is placed in acetic acid, about 2.1 equiv. of zinc oxide (ZnO) is added thereto, and the mixture is stirred at room temperature.

After confirming the conversion of the reaction and termination by TLC, the solid precipitate is removed using a filter, and the remaining acetic acid is removed by evaporation under reduced pressure. Methanol is added to the remaining organic materials, about 2 equiv. of potassium carbonate (K$_2$CO$_3$) is added thereto, and the mixture is refluxed and stirred. When the conversion and termination of the reaction are confirmed by TLC, the reaction temperature is cooled to room temperature. After methanol is removed by evaporation under reduced pressure, the remaining organic materials are distilled under reduced pressure to obtain diol compounds (a mixture of Pa and Ta). On the other hand, according to Reaction Scheme 2-2, it can be confirmed that the amount of Compound Pa is increased compared to that of Compound Ta, so that only Compound Pa is substantially detected (a molar ratio of Compound Pa:Compound Ta is 25:1 or more). Subsequently, an acryloyl group can be introduced into the above mixture of Pa and Ta by the Reaction Scheme 3.

Similarly, the compounds of the Chemical Formulae 1-1 and 1-2 obtained above may be used after separation and purification, or may be used in the form of a mixture without separation.

According to another embodiment of the present disclosure, provided is a polymer obtained by polymerizing the cross-linking agent compound represented by the Chemical Formula 1 and an acrylic acid-based monomer.

The acrylic acid-based monomer is a compound represented by the following Chemical Formula 2:

R—COOM      [Chemical Formula 2]

in Chemical Formula 2,

R is a C2 to C5 alkyl group having an unsaturated bond, and

M is a hydrogen atom, a monovalent or divalent metal, an ammonium group, or an organic amine salt.

Preferably, the acrylic acid-based monomer includes at least one selected from the group consisting of acrylic acid, methacrylic acid, and a monovalent metal salt, a divalent metal salt, an ammonium salt, and an organic amine salt thereof.

Herein, the acrylic acid-based monomers may be those having acidic groups which are at least partially neutralized.

For reference, the term "polymer" or "cross-linked polymer" in the present disclosure means that an acrylic acid-based monomer is polymerized in the presence of the cross-linking agent compound of the Chemical Formula 1, and may cover all moisture content ranges or particle diameter ranges. Among the above polymers, a polymer having a moisture content of about 40 wt % or more after polymerization and before drying can be referred to as a hydrogel polymer.

In addition, the term "base resin" or "base resin powder" refers to a polymer in the form of powder by drying and pulverizing the polymer. And, it refers to a polymer before the surface cross-linking step, so that a cross-linking structure is not formed on the surface of the polymer.

The cross-linking agent compound represented by the Chemical Formula 1 is a pyrolytic internal cross-linking agent. The internal cross-linking structure of the polymer obtained by cross-linking the compound of Chemical Formula 1 and the acrylic acid-based monomer can be decomposed by heat (for example, at 150° C. or higher). Accordingly, when the acrylic acid-based monomer is cross-linked and polymerized in the presence of the cross-linking agent compound of Chemical Formula 1, a cross-linked polymer in which a pyrolytic internal cross-linking structure is introduced can be provided.

Thereafter, when the cross-linked polymer is introduced into a subsequent step at a high temperature such as a surface cross-linking step, the cross-linked structure of the cross-linked polymer derived from the compound of Chemical Formula 1 is at least partially decomposed. As a result, the internal cross-linking density of the cross-linked polymer is reduced. On the other hand, the surface of the cross-linked polymer is further cross-linked by a surface cross-linking agent, thereby increasing external cross-linking density. Therefore, when a base resin is prepared by cross-linking an acrylic acid-based monomer in the presence of an internal cross-linking agent represented by the Chemical Formula 1, and is subjected to a subsequent step such as surface cross-linking, the internal cross-linking structure in the cross-linked polymer is decomposed and the surface of the cross-linked polymer is further cross-linked to obtain a super absorbent polymer in which the cross-linking density increases from inside to outside of the resin.

The super absorbent polymer thus prepared may have reduced internal cross-linking density than the base resin of the conventional super absorbent polymer. Accordingly, the super absorbent polymer can exhibit relatively improved water retention capacity compared with the conventional super absorbent polymer. In addition, the super absorbent polymer may have a thicker surface cross-linked layer than the conventional super absorbent polymer, since the surface cross-linking proceeds after or during decomposition of the internal cross-linking. Thus, the super absorbent polymer can exhibit excellent absorption ability under pressure. Therefore, unlike the conventional common sense that the water retention capacity and the absorption ability under pressure are inversely proportional to each other, the super absorbent polymer of one embodiment increases in cross-linking density from inside to outside and various physical properties such as water retention capacity and absorption ability under pressure are improved together, and thus excellent properties can be exhibited.

In addition, the polymer may be obtained by further polymerizing a conventionally known internal cross-linking agent in addition to the cross-linking agent compound of the above Chemical Formula 1.

As the conventional internal cross-linking agent, a compound containing two or more cross-linkable functional groups in the molecule can be used. A specific example thereof include at least one selected from the group consisting of N,N-methylenebisacrylamide, trimethylolpropane tri(meth)acrylate, ethylene glycol di(meth)acrylate, polyethylene glycol (meth)acrylate, propylene glycol di(meth)acrylate, polypropylene glycol (meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentaacrylate, glycerin tri(meth)acrylate, pentaerythritol tetraacrylate, triarylamine, ethylene glycol diglycidyl ether, propylene glycol, glycerin, and ethylene carbonate, but the present disclosure is not limited thereto.

As described above, the polymer according to the present disclosure has a structure in which a part of the pyrolytic internal cross-linking structure is partially decomposed in the subsequent process at a high temperature after the polymerization due to the characteristics of the novel cross-linking agent compound of Chemical Formula 1, so that the cross-linking density increases from inside to outside of the resin. Therefore, the super absorbent polymer may have excellent properties in which various physical properties such as water retention capacity and absorption ability under pressure are improved together. Further, due to the unique aroma from the structural characteristic of the cross-linking agent compound, it is possible to provide deodorizing effect that reduces the odor peculiar to the super absorbent polymer and/or odors generated when used as hygiene products, and an excellent feeling of use without any additional additive.

Thus, the super absorbent polymer may provide hygiene products such as diapers exhibiting excellent absorption properties and odor characteristics even though it is subjected to a high temperature manufacturing process.

Hereinafter, the function and effect of the present invention will be described in more detail through specific examples of the present invention. However, these examples are for illustrative purposes only, and the invention is not intended to be limited by these examples.

EXAMPLES

Synthesis Examples of Cross-Linking Agent Compound

Synthesis Example 1

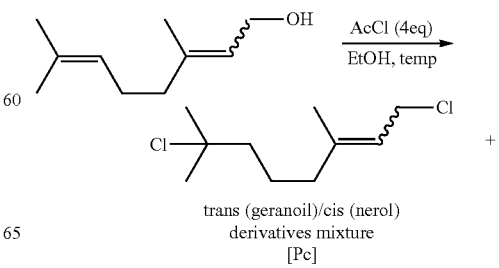

trans (geranoil)/cis (nerol) derivatives mixture
[Pc]

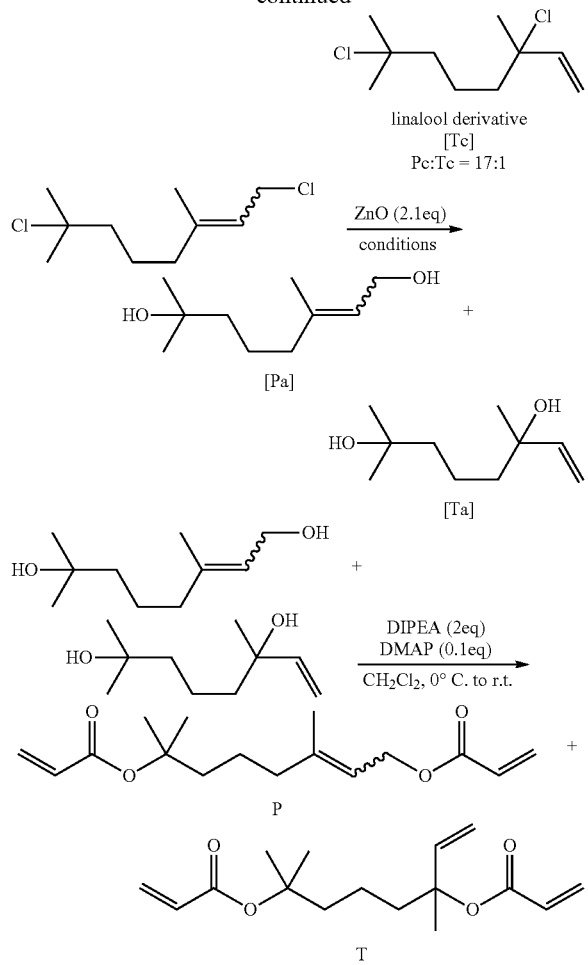

Synthesis Example 1-1

408.7 g of geraniol was dissolved in 700 ml of ethanol and stirred. Acetic chloride (942 g, 856.4 ml, 4 equiv.) was slowly added dropwise while maintaining the reaction temperature at 30° C. When the conversion and termination of the reaction were confirmed by TLC, the solvent and the unreacted materials were removed by evaporation under reduced pressure. The obtained dichloronate compounds (a mixture of Pc and Tc) were used in the next reaction without any further purification.

Pc (CDCl$_3$, 500 MHz): 5.50-5.45 (m, 1H), 4.13-4.07 (m, 2H), 2.16-2.06 (m, 2H), 1.83-1.53 (m, 13H)

Tc (CDCl$_3$, 500 MHz): 6.00 (dd, J=16.87, 11.00, 1H) 5.27 (d, J=16.87, 1H), 5.12 (d, J=11.00, 1H), 2.16-2.06 (m, 2H), 1.83-1.53 (m, 13H).

Synthesis Example 1-2

The dichloronate compounds (a mixture of Pc and Tc, 522.9 g, reference material) obtained in Synthesis Example 1-1 were put into an acetone aqueous solution (1.5 L) of about 80% purity, ZnO (427.2 g, 2.1 equiv.) was added, and the mixture was refluxed at a temperature of 100° C. When the conversion and termination of the reaction were confirmed by TLC, the temperature was cooled to room temperature. Thereafter, the solid precipitate was removed using a filtration filter, and the remaining acetone was removed by evaporation under reduced pressure. The remaining organic material and a small amount of water were removed by fractional distillation to obtain desired diol compounds (a mixture of Pa and Ta).

Pa (CDCl$_3$, 500 MHz): 5.43-5.41 (m, 1H), 4.17-4.12 (m, 2H), 2.12-1.97 (m, 2H), 1.75-1.13 (m, 13H)

Ta (CDCl$_3$, 500 MHz): 5.91 (dd, J=17.10, 10.52, 1H) 5.22 (d, J=17.09, 1H), 5.07 (d, J=10.52, 1H), 2.06-1.97 (m, 2H), 1.76-1.13 (m, 13H).

Synthesis Example 1-3

The diol compounds (51.7 g, reference material) obtained in Synthesis Example 1-2 were dissolved in CH$_2$Cl$_2$ (300 ml) and the temperature was lowered to 0° C. while stirring. After N,N-diisopropylethylamine ((DIPEA, 2 equiv.) and 4-dimethylaminopyridine (7.3 g, 0.1 equiv.) were added, acryloyl chloride (57.0 g, 51.0 ml, 2.1 equiv.) was slowly added thereto. After the addition was completed, the reaction temperature was raised to room temperature and stirred for about 6 hours. After the reaction was completed, the reaction solution was filtered through a celite pad and the solvent was removed under vacuum. The remaining organic materials were extracted with water and ethyl acetate (EA), and the remaining water in the organic layer was removed using sodium sulfate (Na$_2$SO$_4$). The solids were filtered off and the remaining organic solvent was removed under vacuum to obtain a mixture of 2,6-dimethyloct-7-ene-2,6-diyl diacrylate (Compound T) and 3,7-dimethyloct-2-ene-1,7-diyl diacrylate (Compound P) in a yield of about 61%.

2,6-dimethyloct-7-ene-2,6-diyl diacrylate (CDCl$_3$, 500 MHz): 6.15-5.96 (m, 5H), 5.82-5.71 (m, 2H), 5.18-5.12 (m, 2H), 2.15-2.03 (m, 2H), 1.91-1.17 (m, 13H).

3,7-dimethyloct-2-ene-1,7-diyldiacrylate (CDCl$_3$, 500 MHz): 6.39-6.02 (m, 2H), 6.01-5.80 (m, 2H), 5.75-5.72 (m, 2H), 5.44-5.37 (m, 2H), 4.69-4.65 (m, 2H), 2.15-2.03 (m, 2H), 1.77-1.23 (m, 13H).

Synthesis Example 2

Synthesis Example 2-1

The dichloronate compounds (a mixture of Pc and Tc, 313.7 g, reference material) obtained in Synthesis Example 1-1 were put into acetic acid (2 L), ZnO (256.3 g, 2.1 equiv.) was added, and the mixture was stirred at room temperature. When the conversion and termination of the reaction were confirmed by TLC, the solid precipitate was removed using a filtration filter, and the remaining acetic acid was removed by evaporation under reduced pressure. Methanol (1 L) was added to the remaining organic materials, K$_2$CO$_3$ (470.0 g, 2 equiv.) was added thereto, and the mixture was refluxed and stirred. When the conversion and termination of the reaction were confirmed by TLC, the reaction temperature was cooled to room temperature. After methanol was removed by evaporation under reduced pressure, the remaining organic materials were distilled under reduced pressure to obtain diol compounds (a molar ratio of Compound Pa:Compound Ta was 25:1 or more, so that only Compound Pa was substantially detected).

Pa (CDCl$_3$, 500 MHz): 5.43-5.41 (m, 1H), 4.17-4.12 (m, 2H), 2.12-1.97 (m, 2H), 1.75-1.13 (m, 13H)

Synthesis Example 2-2

The diol compound (Compound Pa, 51.7 g, reference material) obtained in Synthesis Example 2-1 was dissolved in CH$_2$Cl$_2$ (300 ml) and the temperature was lowered to 0° C. while stirring. After triethylamine (91.1 g, 125.4 ml, 3 equiv.) and 4-dimethylaminopyridine (7.3 g, 0.1 equiv.) were added, acryloyl chloride (57.0 g, 51.0 ml, 2.1 equiv.) was slowly added thereto. After the addition was completed, the reaction temperature was raised to room temperature and stirred for about 6 hours. After the reaction was completed, the reaction solution was filtered through a celite pad and the solvent was removed under vacuum. The remaining organic materials were extracted with water and ethyl acetate (EA), and the remaining water in the organic layer was removed using sodium sulfate (Na$_2$SO$_4$). The solids were filtered off and the remaining organic solvent was removed under vacuum to obtain 3,7-dimethyloct-2-ene-1,7-diyl diacrylate (Compound P) in a yield of about 63%.

3,7-dimethyloct-2-ene-1,7-diyldiacrylate (CDCl$_3$, 500 MHz): 6.39-6.02 (m, 2H), 6.01-5.80 (m, 2H), 5.75-5.72 (m, 2H), 5.44-5.37 (m, 2H), 4.69-4.65 (m, 2H), 2.15-2.03 (m, 2H), 1.77-1.23 (m, 13H).

Synthesis Example 3

The mixture of Compound T and Compound P obtained in Synthesis Example 1-3 was separated through chromatography to selectively obtain Compound T.

Synthesis Example 4

Synthesis Example 4-1

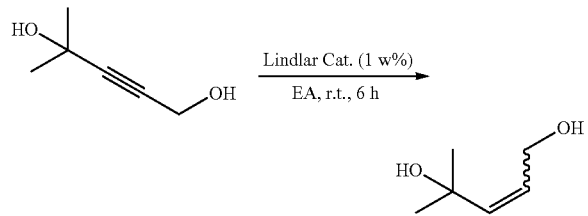

4-methylpent-2-yne-1,4-diol (1 g) was dissolved in ethyl acetate (20 ml) in a 100 ml pressure vessel, and stirred while making nitrogen atmosphere. Lindlar catalyst (10 mg, 1 w %) was carefully added and the pressure vessel was sealed. All the nitrogen in the pressure vessel was replaced with 5 bar of hydrogen and stirred for about 6 hours. After the reaction was completed, the hydrogen was carefully removed and the solid of the reaction solution was removed through a celite filter. The solvent of the filtrate was distilled under reduced pressure to obtain 4-methylpent-2-ene-1,4-diol (650 mg).

Synthesis Example 4-2

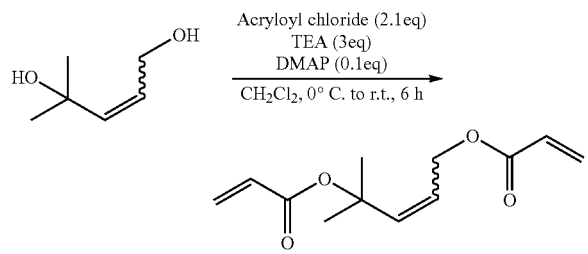

The 4-methylpent-2-ene-1,4-diol (3.5 g, reference material) obtained in Synthesis Example 4-1 was dissolved in CH$_2$Cl$_2$ (30 ml) and the temperature was lowered to 0° C. while stirring. After triethylamine (9.2 g, 12 ml, 3 equiv.) and 4-dimethylaminopyridine (0.7 g, 0.1 equiv.) were added, acryloyl chloride (5.7 g, 5 ml, 2.1 equiv.) was slowly added thereto. After the addition was completed, the reaction temperature was raised to room temperature and stirred for about 6 hours. After the reaction was completed, the reaction solution was filtered through a celite pad and the solvent was removed under vacuum. The remaining organic materials were extracted with water and ethyl acetate (EA), and the remaining water in the organic layer was removed using sodium sulfate (Na$_2$SO$_4$). The solids were filtered off and the remaining organic solvent was removed under vacuum to obtain 4-methylpent-2-ene-1,4-diyl diacrylate in a yield of about 72%.

4-methylpent-2-ene-1,4-diyl diacrylate (CDCl$_3$, 500 MHz): 6.44-6.05 (m, 2H), 6.09-5.86 (m, 2H), 5.75-5.71 (m, 2H), 5.61-5.57 (m, 2H), 4.33-4.22 (m, 2H), 1.39 (m, 6H)

Examples of Preparation of Super Absorbent Polymer

Example 1

100 g of acrylic acid, 123.5 g of 32% sodium hydroxide (NaOH), 0.2 g of sodium persulfate as a thermal polymerization initiator, 0.008 g of diphenyl(2,4,6-trimethylbenzoyl)-phosphine oxide as a photopolymerization initiator, 0.6 g of the cross-linking agent mixture of Synthesis Example 1-3 and 55.0 g of water were mixed to prepare a monomer composition having a total solids concentration of 43.8 wt %.

The monomer composition was fed onto a rotating belt having a width of 10 cm, a length of 2 m, and a rotating speed of 50 cm/min at a feed rate of 500 mL/min to 2,000 mL/min. While feeding the monomer composition, ultraviolet ray having an intensity of 10 mW/cm$^2$ was irradiated to perform a polymerization reaction for 60 seconds. After the polymerization reaction, it was cut by a meat chopper method and dried at 185° C. for 40 minutes using an air-flow oven to prepare a super absorbent polymer (a base resin).

Example 2

A super absorbent polymer was prepared in the same manner as in Example 1 except that 0.6 g of the cross-linking agent compound of Synthesis Example 2-2 was used.

Example 3

A super absorbent polymer was prepared in the same manner as in Example 1 except that 0.6 g of the cross-linking agent compound of Synthesis Example 3 was used.

Example 4

A super absorbent polymer was prepared in the same manner as in Example 1 except that 0.6 g of the cross-linking agent compound of Synthesis Example 4-2 was used.

Comparative Example 1

A super absorbent polymer was prepared in the same manner as in Example 1 except that 0.26 g of polyethylene glycol diacrylate (PEGDA) was used as an internal cross-linking agent.

Experimental Examples

Evaluation of Pyrolysis of Super Absorbent Polymer

In order to evaluate pyrolysis at high temperature and a change in absorption ability of the polymer obtained by polymerizing the cross-linking agent compound of the present disclosure and the acrylic acid-based monomer, the super absorbent polymers of Examples and Comparative Examples were subjected to heat treatment at 185° C., and the change in centrifuge retention capacity over time was measured and listed in Table 1 below.

(1) Centrifuge Retention Capacity (CRC)

The centrifuge retention capacity (CRC) to a saline solution of the super absorbent polymer was measured according to EDANA WSP 241.3.

Specifically, a sample of the super absorbent polymer having a particle diameter of 150 to 850 μm, which is passed through a US standard 20 mesh screen and is kept on a US standard 100 mesh screen, was prepared from a super absorbent polymer to be tested for centrifugal retention capacity.

Thereafter, W0(g) (about 0.2 g) of the sample having a particle diameter of 150 to 850 μm was uniformly placed into a non-woven bag, and sealed. Then, it was immersed in 0.9 wt % sodium chloride aqueous solution (physiological saline) at room temperature. After 30 minutes, water was drained from the bag by centrifugal device under the condition of 250 G for 3 minutes, and the weight W2(g) of the bag was measured. In addition, the same manipulation was performed for an empty bag without the sample, and the weight W1(g) of the bag was measured.

The CRC was calculated by using the obtained weight values according to the following Equation 1.

$$CRC\ (g/g) = \{[W2(g) - W1(g)]/W0(g)\} - 1 \quad \text{[Equation 1]}$$

In Equation 1,

W0(g) is an initial weight (g) of the sample having a particle diameter of 150 to 850 μm, W1(g) is a weight of the empty non-woven bag measured after immersing the non-woven bag without the sample in a saline solution for 30 min at room temperature and dehydrating the same by using a centrifuge at 250 G for 3 min, and W2(g) is a weight of the non-woven bag with the sample measured after immersing the non-woven bag with the sample in a saline solution for 30 min at room temperature and dehydrating the same by using a centrifuge at 250 G for 3 min.

TABLE 1

| | Heat treatment time (min, 185° C.) | CRC(g/g) |
|---|---|---|
| Example 1 | 0 | 66.0 |
| | 20 | 68.0 |
| | 40 | 69.0 |
| | 60 | 69.4 |
| Example 2 | 0 | 72.6 |
| | 20 | 79.6 |
| | 40 | 81.4 |
| | 60 | 81.8 |
| Example 3 | 0 | 66.0 |
| | 20 | 68.0 |
| | 40 | 69.0 |
| | 60 | 69.4 |
| Example 4 | 0 | 70.2 |
| | 20 | 77.3 |
| | 40 | 79.2 |
| | 60 | 80.7 |

TABLE 1-continued

| | Heat treatment time (min, 185° C.) | CRC(g/g) |
|---|---|---|
| Comparative Example 1 | 0 | 50.2 |
| | 20 | 51.9 |
| | 40 | 50.6 |

Referring to Table 1, in the case of Examples 1 to 4 in which acrylic acid-based monomer was cross-linked in the presence of the novel cross-linking agent compound of Chemical Formula 1, when heat treatment was performed at a high temperature (185° C.), the water retention capacity increased with time. This may be because the internal cross-linking structure of the polymer was decomposed by the high temperature to lower the cross-linking density.

On the other hand, Comparative Example 1 using the conventional cross-linking agent did not show a significant increase in the water retention capacity with the heat treatment time.

What is claimed is:

1. A cross-linking agent compound represented by the following Chemical Formula 1:

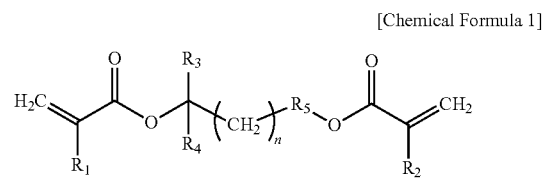

[Chemical Formula 1]

wherein in Chemical Formula 1, $R_1$ and $R_2$ are each independently hydrogen or methyl, $R_3$ and $R_4$ are each independently a C1 to C20 alkyl, $R_5$ is a linear or branched C1 to C20 alkylene substituted with a linear or branched C2 to C10 alkenyl; or a linear or branched C2 to C20 alkenylene, and n is an integer of 0 to 10.

2. The cross-linking agent compound of claim 1, wherein the $R_1$ and $R_2$ are hydrogen.

3. The cross-linking agent compound of claim 1, wherein the $R_3$ and $R_4$ are a C1 to C5 alkyl.

4. The cross-linking agent compound of claim 3, wherein the $R_3$ and $R_4$ are methyl.

5. The cross-linking agent compound of claim 1, wherein the R5 is a linear or branched C1 to C10 alkylene substituted with a linear or branched C2 to C10 alkenyl; or a linear or branched C2 to C10 alkenylene.

6. The cross-linking agent compound of claim 5, wherein the R5 is selected from the group consisting of 3-methyl-2-hexenylidene, 3-methyl-1-hexenylidene, and 4,8-dimethylundeca-3,7-dienylene.

7. The cross-linking agent compound of claim 1, wherein the compound of Chemical Formula 1 is selected from the compounds represented by the following Chemical Formulae 1-1 to 1-3:

[Chemical Formula 1-1]

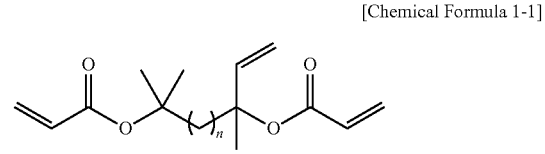

[Chemical Formula 1-2]

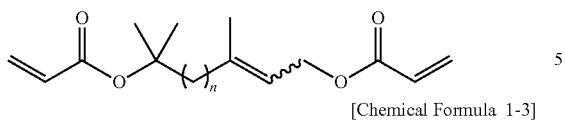

[Chemical Formula 1-3]

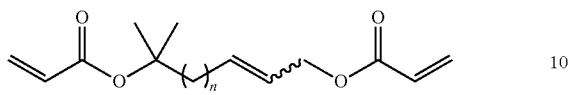

wherein in Chemical Formulae 1-1 to 1-3, n is as defined in the Chemical Formula 1.

8. The cross-linking agent compound of claim 1, wherein the cross-linking agent compound is prepared from myrcene or geraniol as a starting material.

9. A polymer obtained by polymerizing the cross-linking agent compound of claim 1 and an acrylic acid-based monomer.

10. The polymer of claim 9, wherein the acrylic acid-based monomer is a compound represented by the following Chemical Formula 2:

$$R\text{—}COOM \quad \text{[Chemical Formula 2]}$$

wherein in Chemical Formula 2,

R is a C2 to C5 alkyl group having an unsaturated bond, and

M is a hydrogen atom, a monovalent or divalent metal, an ammonium group, or an organic amine salt.

* * * * *